United States Patent [19]

Davidson et al.

[11] 4,389,670
[45] Jun. 21, 1983

[54] ELECTRONIC METHOD FOR AUTOFLUOROGRAPHY OF MACROMOLECULES ON TWO-D MATRICES

[75] Inventors: Jackson B. Davidson; Arthur L. Case, both of Oak Ridge, Tenn.

[73] Assignee: The United States of America as represented by the United States Department of Energy, Washington, D.C.

[21] Appl. No.: 335,998

[22] Filed: Dec. 30, 1981

[51] Int. Cl.$^3$ ............................................. H04N 7/18
[52] U.S. Cl. ................................ 358/111; 235/92 PC; 358/107; 358/211; 250/363 R; 376/159
[58] Field of Search ................... 358/111, 107, 211; 235/92 PC; 378/49

[56] References Cited

U.S. PATENT DOCUMENTS 4,319,271  3/1982  Hurni ............................. 235/92 PC

OTHER PUBLICATIONS

N. Wade, "The Complete Index to Man," *Science*, 211, 33–35 (Jan. 2, 1981).
E. P. Lester et al, "Computer Assisted Analysis of Two-Dimensional Electrophoreses of Human Lymphoid Cells," *Clinical Chemistry*, 26(10), 1392–1412 (1980).
V. W. Arndt et al, "X-ray Television Area Detectors for Macromolecular Structural Studies with Synchrotron Radiation Sources", *Journal of Applied Crystalography* (1979) 12, pp. 1–9.

*Primary Examiner*—Howard Britton

[57] ABSTRACT

A method for detecting, localizing, and quantifying macromolecules contained in a two-dimensional matrix is provided which employs a television-based position sensitive detection system. A molecule-containing matrix may be produced by conventional means to produce spots of light at the molecule locations which are detected by the television system. The matrix, such as a gel matrix, is exposed to an electronic camera system including an image-intensifier and secondary electron conduction camera capable of light integrating times of many minutes. A light image stored in the form of a charge image on the camera tube target is scanned by conventional television techniques, digitized, and stored in a digital memory. Intensity of any point on the image may be determined from the number at the memory address of the point. The entire image may be displayed on a television monitor for inspection and photographing or individual spots may be analyzed through selected readout of the memory locations. Compared to conventional film exposure methods, the exposure time may be reduced 100–1000 times.

9 Claims, 3 Drawing Figures

ELECTRONIC METHOD FOR AUTOFLUOROGRAPHY OF MACROMOLECULES ON TWO-D MATRICES

BACKGROUND OF THE INVENTION

This invention is a result of a contract with the United States Department of Energy and it relates generally to methods for detecting and quantifying labeled macromolecules disposed in a mapped array on a matrix and more specifically relates to an electronic method for separately detecting and quantifying labeled macromolecules disposed in a mapped array on a matrix and provides direct digital storage of such information.

Many biological research laboratories are investigating normal and abnormal, human, and animal proteins using one- and two-dimensional separation techniques to produce protein maps of plasma, urine, etc. Projects to compile a complete protein index of humans are also underway. Other laboratories are using recombinant DNA techniques to study the basic properties of DNA and to manipulate DNA fragments to "engineer" organisms that can manufacture scarce substances such as insulin, growth hormone, and interferon. Still others seek to distinguish tissues, particularly tumors or to detect genetic diseases. Essential to much of this research and development are the sequence analysis of the DNA fragments and the screening of clones for specific genes. Both techniques require the detection of radioactive nucleic acid or antibody using autoradiography.

The projects and techniques mentioned above use autoradiography or autofluorography in which X-ray film is exposed for hours or days in order to visualize the distribution and the amounts of labeled macromolecules. Quantitation of activity is done by visual estimation or by densitometry. In some laboratories optical scanning of the film is done by mechanical or television techniques which transmit the data to the computer for analysis and comparison. In addition to the long exposure time, factors associated with film are nonlinearity, difficult reproducibility in manufacture and development, fogging, and dynamic range.

The direct detection of activity of $^3H$, $^{14}C$, $^{35}S$ and $^{32}P$ labeled 2-D gels has been done with one- and two-dimensional spark chambers and proportional counters. The low energy of the betas from some isotopes requires that very thin windows be used or that the gel be placed inside the counter, with the risk of contamination of the counting gas, distorting the electric field due to charging of the gel, etc. In these counters the betas must leave the gel to be detected, causing a loss of efficiency at lower energies. Another way is to scan the gel with a point or slit detector, using a G.M. tube or a scintillation counter. Also, the gel can be cut into small pieces which are counted individually in a liquid-scintillation counter.

One form of autofluorography is a technique in which a scintillant is incorporated into the gel. This allows the weak betas from $^3H$, for example, to be detected in situ by the light they produce, since the light, unlike beta particles, can penetrate the gel and interact with the film. Although this method has reduced the exposure time for exposing photographic film to a matter of days and weeks as opposed to periods much longer for autoradiography using X-ray film which is exposed directly from the beta emissions, this is still a very long time to provide a readout of the gels and does not overcome the other disadvantages of the film. An increase in sensitivity as well as an improvement in linearity of autofluorography may be obtained by pre-exposure of the film, however, the amount of pre-exposure must be carefully optimized, to obtain linearity. At the optimum pre-exposure for linearity, there is obtained a sensitivity increase of about four times over autofluorography without pre-exposure of the film. At the optimum pre-exposure for sensitivity the increase is about ten times but with non-linearity at higher activity levels.

In mapping studies of complex large molecules such as proteins, one of the most practical techniques is a two-dimensional gel matrix in which the molecules are distributed on the matrix by a process known as electrophoresis. The proteins extracted from a selected human tissue or body fluid, for example, are separated in one dimension according to their electric charge and in a second (perpendicular) dimension according to their molecular weight. The result is a complex two-dimensional map, often of more than 1000 distinguishable spots. These gels must be scanned or otherwise examined: (1) with visible light after staining or by ultraviolet excited fluorescence; or (2) by the assimilation of radioactive tracers in the molecules followed by two-dimensional detection of the radioactivity using film methods as described above.

The information desired of these two-dimensional molecular distributions is two-fold. First, the gross amounts of protein in the spots and location of the spots on the two-dimensional gel matrix need to be determine. Second, the gross amount of radioactivity taken up by the proteins is also desired.

In these applications, it may take hours or days to produce the two-dimensional gels through electrophoresis. Following this, recording of the spot activities with photographic film as pointed out above may take additional hours or days to obtain adequate exposures for identification and quantification of the distributed molecules. In addition to being very time consuming, the film methods also suffer from linearity of response as pointed out above.

Thus, there is a need for a direct method of detecting and quantifying distributed molecules on a matrix which does not require the time consuming step of exposure of a photographic film and dealing with its inherent disadvantages.

SUMMARY OF THE INVENTION

In view of the above need, it is an object of this invention to provide an electronic based method for improved two-dimensional detection of macromolecules distributed on a matrix which eliminates the time consuming photographic film exposure techniques.

Another object of this invention is to provide a television-based method for detecting quantifying and digitally storing information relative to the distribution pattern of labeled macromolecules on a matrix in a few seconds or minutes.

Additional objects, advantages, and novel features of the invention will be set forth in part in the description which follows and in part will become apparent to those skilled in the art upon examination of the following or may be learned by practice of the invention. The objects and advantages of the invention may be realized and obtained by means of the instrumentalities and combinations particularly pointed out in the appended claims.

To achieve the foregoing and other objects and in accordance with the purpose of the present invention, as embodied and broadly described herein, the method of this invention may comprise an autofluorographic method of detecting and quantifying labeled macromolecules resolved on a matrix in which light spots are produced which correspond to the location and quantity of said macromolecules in said matrix. The light-emitting matrix is exposed to a lensless, intensified television camera system having an electron sensitive target on which an electric charge image is accumulated corresponding to the light pattern image of the matrix viewed by the camera. The target is subsequently scanned in a television raster with an electron beam to remove the accumlated charge image from the target. The output signals from the camera tube may be digitized and stored in a digital memory device which is addressed according to the location of the light intensities on the matrix.

The macromolecules may be labeled by radioactive elements incorporated in the molecules which excite scintillations in a scintillating material incorporated in the matrix in which the light from scintillations are viewed by camera.

In another embodiment, the molecules may be labeled by means of a stain which phosphoresces or fluoresces when excited by an appropriate light source and the phosphorescence or fluorescence is subsequently viewed by the television camera to resolve the light pattern image and thus the location of the molecules and their quantity on the matrix.

This electronic method compared to the prior art film exposure method reduces the time for exposure from 100–1000 times. The response to low activity levels is improved and spatial resolution is maintained.

DESCRIPTION OF THE DRAWINGS

The accompanying drawings, which are incorporated in and form a part of the specification illustrate two embodiments of a system for carrying out the method of the present invention and, together with the description, serve to explain the principles of the invention.

In the drawings.

DETAILED DESCRIPTION OF THE INVENTION

Figure 1:
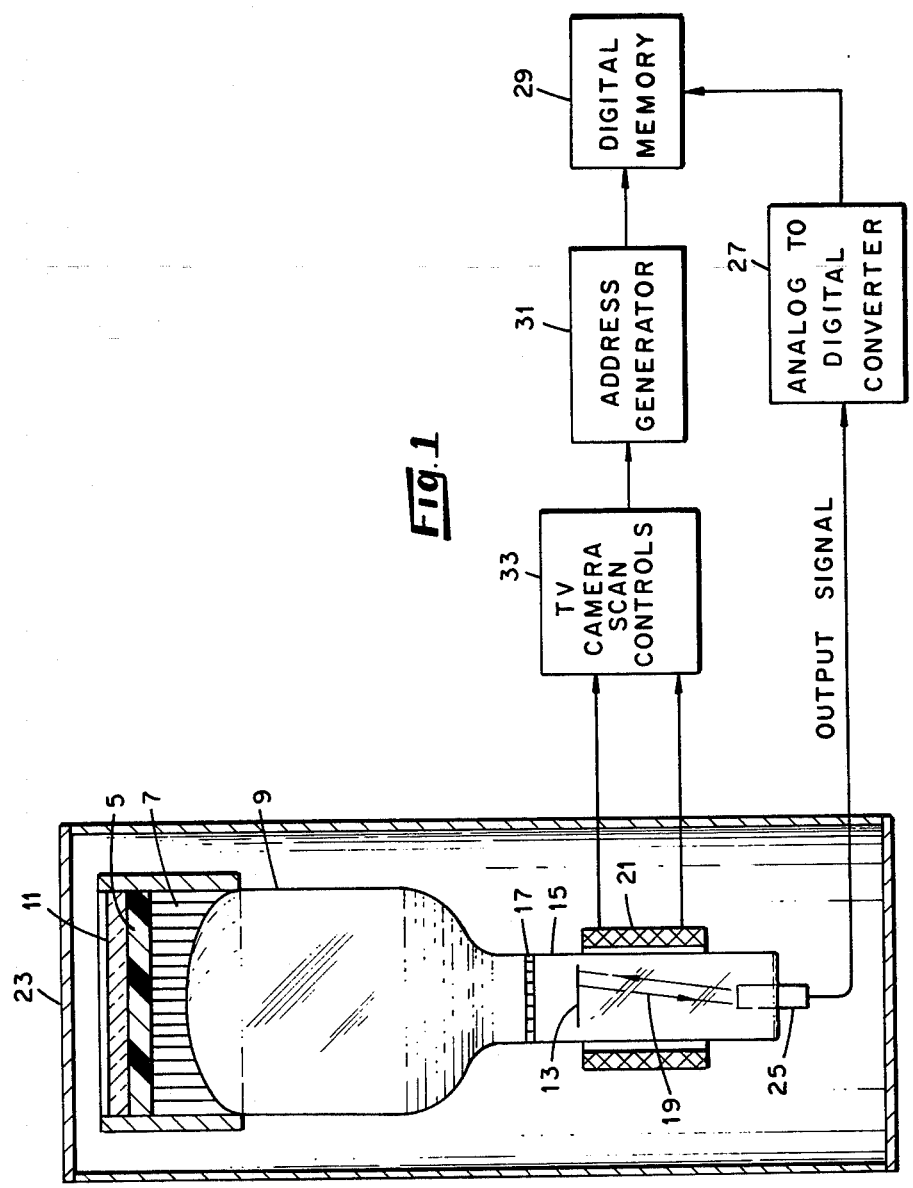
FIG. 1 is a schematic block diagram of a television-based system for carrying out the method of the subject invention.

Referring now to FIG. 1, there is shown a televsion-based system for autofluorographically detecting and quantifying labeled macromolecules contained on a two-dimensional matrix 5. The matrix may take various forms such as a polyacrylamide gel sheet onto which the molecules are resolved by means of techniques known as electrophoresis and/or chromatography into a two-dimensional ordered array on the gel sheet. The gel sheet may include a scintillating material integral with the gel which allows the emissions from the radioactively labeled molecules to produce light in the scintillator material in the areas where the molecules are concentrated. The light is then detected by the television camera. Obviously, other matrix materials, such as silica gels, alumina plates, various filter papers, etc. on which the molecules are resolved may be used. Further, various other means to label the molecules, such as by visible, fluorescent and/or phosphorescent stains, will be described hereinbelow.

As shown in FIG. 1, the matrix 5 containing the labeled macromolecules is positioned on a fiber-optic face plate 7 which is attached to the light receiving end of an image-intensifier 9. The fiber optics plate 7 collimates the light generated in the gel matrix 5 and prevents scattering of the light spot prior to entering the intensifier 9. The gel matrix 5 may be held tightly against the fiber optics plate 7 by means of a transparent quartz pressure plate 11 placed over the gel plate or by vacuum.

The image intensifier 9 provides the required sensitivity for detecting the low light levels (10–1000 photons) emitted by the scintillator material in the matrix 5. The intensified light pattern is converted to an electric charge image on the target 13 from the intensifier of a television camera tube 5 in a conventional manner through an optical coupler 17. This allows measurement of the entire matrix 5 area at the same time by focusing the light pattern image from the matrix onto the target 13 with a spatial resolution comparable to the photographic film method. The television camera tube operates as a two-dimensional detector equivalent to 100,000 or more detectors operating simultaneously. The resolution will of course depend on the addressable increments along each scan line of the target 13 as the charge image of the light pattern image stored thereon is removed in a conventional television camera scanning arrangement. Further, the light integrating property of film as in a time exposure may be duplicated in the target operation by allowing charge to accumulate for a longer period of time than that required to scan the target 13 by turning the scan beam 19 "off". The beam may be turned off for preselected times according to the desired integrating time. This enables time exposures to be taken and the integrated images of the radioactive response in the matrix 5 to be stored on the target 13 electronically, taking advantage of the properties of increased sensitivity and exposure linearity of the television camera tube target before readout by the scanning electron beam 19. Given the improved sensitivity, total area capability, and integrating property, the time required to acquire data is reduced by orders of magnitude (100–1000 times) over conventional photographic film exposure methods with greatly improved linearity as will be discussed hereinbelow.

To prevent stray light from interfering with the measurement, the entire camera may be enclosed in a light-tight enclosure 23 with access to insert and remove the matrix 5 from a holder arrangement at the face of the image intensifier.

The analog signal from the camera tube is amplitude modulated corresponding to the stored charge intensity on the target encountered by the electron beam from the electron gun 25 of the television camera tube as it scans the target 13 in a raster. It will be understood that the output signal together with the proper synchronizing scanning controls of a conventional television system may also be supplied to a conventional television monitor for direct readout of the matrix light pattern image in real time. This could also allow direct viewing of the movement of the molecules as they are resolved on the matrix by altering the camera viewing arrangement.

To digitally store the information for readout of individual light spots or subsequent viewing of the entire light pattern on a television monitor for analysis, analog signal output is converted to a digital signal by means of an analog-to-digital converter 27 and put in a digital memory 29. Addresses for each of the incremental locations along the entire scan path are generated by means of an address register 31. The address register 31 is maintained in synchronization with the camera target scanning signal from a television camera scanning control system 33. The control system 33 may be a conventional television scanning control which supplies signals to the horizontal and vertical beam scanning control yokes 21. The address generator 31, analog-to-digital converter 27 and digital memory 29 may comprise a commercially available digital readout and storage device for use with a television camera, such as the Model D5-20 manufactured by Quantex Corp, Sunnyvale, Calif.

By this means, the original image is converted into an array of numbers, each number being assigned to a given point in the image. The digital memory thus provides for the necessary quantification of the activity by the stored digital signal value as well as its accurate spatial location. Data manipulation such as background subtraction, intercomparisons (as in metabolic and catabolic rate studies), and radioactivity uptake, calculations and so forth, may be performed using digital computer means.

One form of the method of the invention will be described in detail in the following example.

EXAMPLE

A polyacrylamide gel matrix containing $^3$H-labeled proteins together with a scintillant 2,5-diphenyloxazole (PPO) incorporated in the gel, which had been previously prepared for X-ray film exposure, was exposed to a camera system as shown in FIG. 1. The scanning electron beam, which reads the integrated signal from the camera tube target, was turned off during an integrating period of about 2 minutes for each exposure. At the end of the integrating time, the stored image of the gel was scanned, digitized with an 8-bit analog-to-digital converter in 0.33 seconds, and stored in a computer-controlled digital memory of 512 by 512, 12-bit words. The intensity of any point in the image could be determined from the number at the memory address of the point. The entire image was displayed on a television monitor for inspection and photographing. The autofluorographic film image from the electrophoresed gel and the image generated from digital memory and photographed from the television screen was carefully compared. After an electronic exposure of only 2 minutes, the images are comparable in visible detail and resolution, although the exposure time for the electronic method was over 1400 times less. Easily recognizable and measurable features were visible after one minute.

Figure 2:
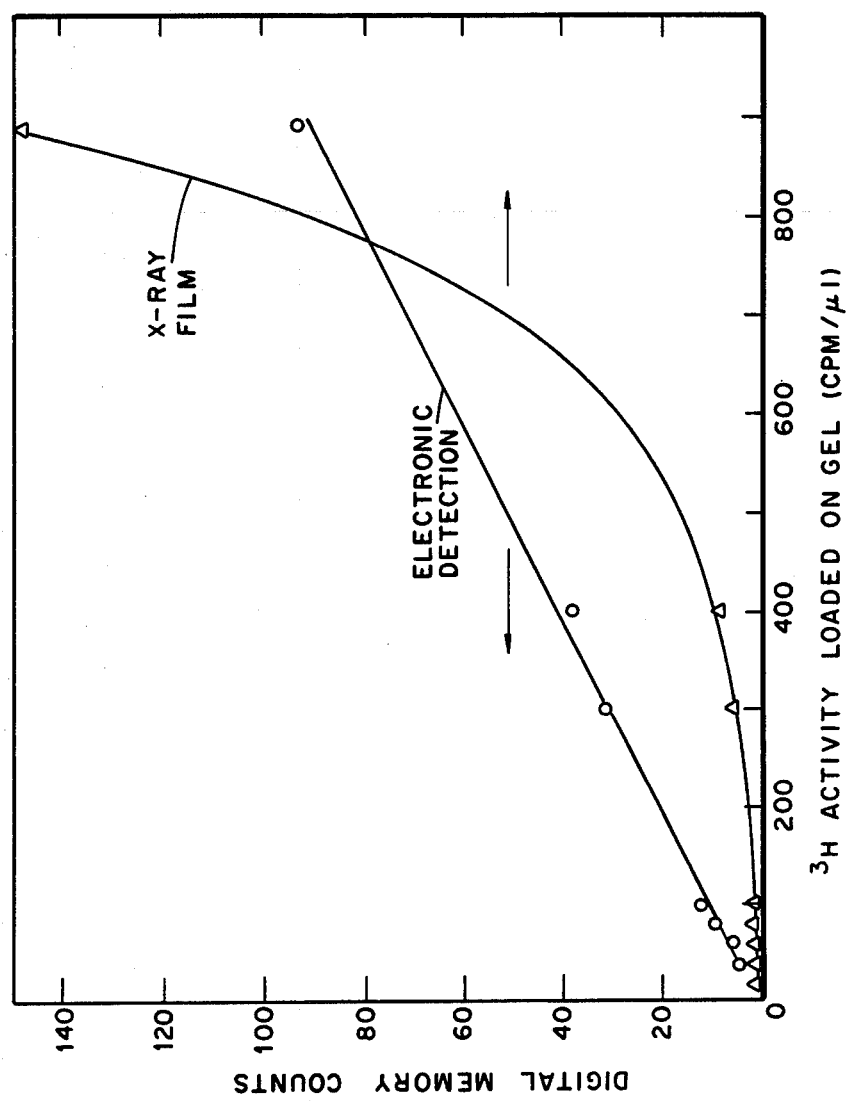
FIG. 2 is a graph illustrating the improvement in linearity of exposure in the present television-based system as compared to the prior art film exposure method.

The gel contained a calibration strip consisting of tritiated segments loaded with 20, 40, 60, 80, 100, 200, 300, and 890 counts per minute per microliter of gel solution. The strip was exposed to film, and to the television-based system of the present invention. The curves of FIG. 2 are a comparison of the response of the electronic technique to that of the X-ray film. The film was measured on a densitometer. The same tritium- and scintillant-containing test strips were used for both curves. The exposures in this experiment were 34 minutes for the electronic method (the sum of 17 two-minute exposures) verses 48 hours at 23° C. for the X-ray film. The improved linearity of the response from the electronic curve is evident. The curves of FIG. 2 show the non-linearity of the film calibration and its insensitivity to changes in low levels of activity. The television-based method gives a linear response.

From these results it will be appreciated that a new method for rapid and improved quantitation of low-energy beta emitting isotopes used in chromatography and electrophoresis is provided. Furthermore, isotopes such as $^{55}$Fe, $^{125}$I, or $^{51}$Cr which emit Auger electrons, or fluorescent x-rays should be amenable to this technique. Higher-energy beta particles such as from $^{32}$P and electron captured gammas may be detected with interposed phosphors and conversion layers. The greatly increased sensitivity permits the use of much less radioactivity, which may lower the cost and ease the problem of radioactive waste disposal. In addition smaller beginning amounts of protein should improve the resolution of closely spaced spots.

Since light is the agent which enables the particles to be detected, the method can be adapted for quantitation of fluorescence and visible light absorption introduced by selective staining. For example, the molecules which are resolved on a gel, or other matrices, may be labeled with a fluorescent and/or phosphorescent material or stain. Stains, such as Coomassie blue, which become visible in white light may be applied to the gel and taken up selectively by protein molecules, for example. The stain may be detected by backlighting the gel with white light. Other stains which fluoresce when excited by ultraviolet light, such as fluorescein or napthol yellow, may be used to label the molecules. Since the image intensifier of the camera tube may be rendered insensitive to ultraviolet light, it provides a good signal-to-noise ratio of the measured spots. The measured variable here is the amount of fluorescence or phosphorescence given off by the molecules of interest together with their location.

Figure 3:
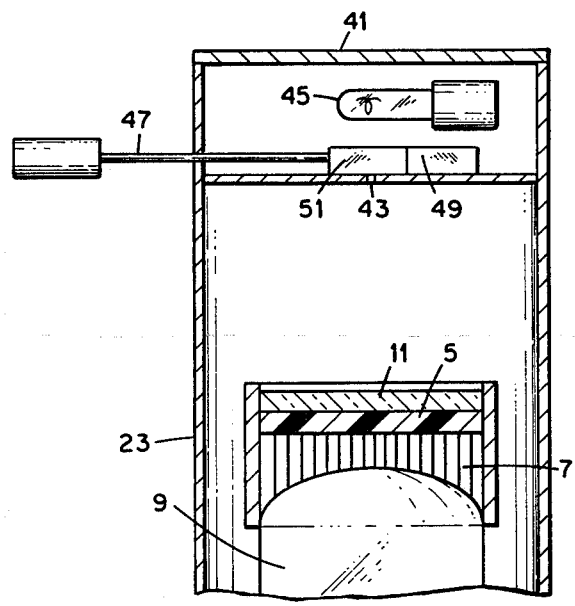
FIG. 3 is a drawing illustrating an arrangement for exciting stain-labeled molecules on a matrix in which an alternate method for carrying out the invention may be practiced. An ultraviolet and/or visible light source is used to backlight the matrix to excite selected stain-labeled molecules resolved on the matrix.

To make these types of measurements, the upper part of the light tight housing 23 may be altered as shown in FIG. 3, wherein like reference numerals refer to like parts as shown in FIG. 1. As shown, the upper part of housing 23 is extended to form a light chamber 41 above the light receiving end of the image intensifier 9. The bottom wall of the chamber 41 has a small aperture 43 therein to allow light from a light source 45 which emits both visible and ultraviolet rays to fall on the gel plate 5. A pair of filters, 49 and 51, are slidably disposed to be moved over the aperture 43 by means of a manual filter control slide assembly 47 having a handle which extends outside the chamber 41. This allows an operator to selectably expose strain-labeled molecules on a matrix 5 to be excited by either ultraviolet or visible light. The excited molecules in the gel are exposed to the television camera for readout in the same manner as described above. Depending upon the type of stain used the readout by the camera tube may be either simultaneous with, or following exposure of the molecules on the gel to the exciting light source.

In cases where higher energy beta-emitting isotopes are used for labeling (e.g., $^{14}C$, $^{35}C$, $^{32}p$), an external phosphor may be interposed between the matrix and the fiber optics face plate of the image intensifier 9. This phosphor acts as an interacting substance for the beta particles that have sufficient energy to leave the gel and produce light photons in the phosphor. If any low energy betas are present, the light from their interaction in the matrix may be blocked from the external phosphor by means of a thin absorber such as aluminized mylar placed between the gel and the phosphor. For example, in studying the rates of synthesis of ribonucleic acid (RNA) and desoxyribonucleic acid (DNA) the starting components are labeled with different isotopes such as $^3H$ and $^{32}p$. After separating the molecules in two dimensions by electrophoresis as described above, RNA and DNA can be distinguished by this blocking technique and rates determined.

Alternatively, chemical elements may be used which are taken up by the large molecules on the matrix whose distribution is to be determined. A chemical element is activated (i.e., caused to be radioactive, by neutron bombardment from a neutron source). The neutron activated chemical element may be detected in a manner similar to that described earlier for either a built-in scintillator or an external phosphor. Here, also, the internal scintallator and/or external phosphor would be selected on the basis of the energy of induced activity. For example, a highly sensitive silver stain is currently in use in many laboratories. The use of this stain involves a photographic development process to make the silver visible in white light. In the present alternative the stained and developed layer would be exposed to neutrons from a reactor or other source and the isotope/isotopes, for example $47Ag^{110M}$, located and measured by the present method.

Thus, it will be seen that a very useful method has been provided for autofluorographic analysis of labeled macromolecules resolved in a matrix. The foregoing description of preferred forms of the method of this invention has been presented for purposes of illustration and description. It is not intended to be exhaustive or to limit the invention to the precise form disclosed, and obviously many modifications and variations are possible in light of the above teaching. For example, although a gel matrix has been described throughout the present disclosure, the system is not limited to electrophoretically produced molecular distributions. Paper or other substances such as are used in paper chromatography, thin layer chromatography, and the like may also be employed as a separation medium and similarly detected, localized, and quantified. In either case the direct entry of spatial distribution information and amount may be entered into digital memory with the same reduction of time to acquire data over the prior art film methods. That reduction in time being a factor of 100–1000 compared to present film techniques. The forms of the invention were chosen and described in order to best explain the principles of the invention and its practical applications thereby to enable others skilled in the art to best utilize the invention in various forms and with various modifications as are suited to the particular application. It is intended that the scope of the invention be defined by claims appended hereto.

What is claimed is:

1. An autofluorographic method of detecting and quantifying labeled macromolecules resolved in a matrix in which light spots are produced which correspond to the location and quantity of said macromolecules in said matrix, including the steps of:

exposing said matrix to a television camera system having a lensless, intensified, light sensitive target means on which an electric charge image is accumulated corresponding to said light patterns of said matrix;

scanning said target in a raster with an electron beam to remove the accumulated charge image from said target, and producing output signals indicative of the location and quantity of the electric charge removed from said charge image on said target.

2. The method of claim 1 wherein the exposure step further includes exposing said camera to said light patterns of said matrix for a preselected period to integrate the light emitted from said matrix prior to said scanning step.

3. The method of claim 1 further including the steps of converting said output signals to digital signals and storing said digital signals in a digital memory.

4. The method of claim 1 wherein said matrix includes a gel sheet having a scintillating material incorporated therein and wherein said macromolecules are radioactivity labeled to produce scintillations in said matrix at the locations of said macromolecules in said gel sheet.

5. The method of claim 4 wherein said matrix is formed of a polyacrylamide gel sheet and said macromolecules are tritium labeled proteins.

6. The method of claim 1 wherein said macromolecules are labeled with a fluorescent strain and further including the step of directing a source of light on said matrix to excite fluorescence of said stained molecules prior to exposing said matrix to said camera.

7. The method of claim 1 wherein said macromolecules are labeled with a phosphorescent stain.

8. The method of claim 1 wherein said macromolecules are labeled by induced radioactivity from neutron bombardment.

9. The method of claim 1 wherein said macromolecules are labeled with a stain that becomes visible in white light, and further including the step of directing a source of white light on said matrix during exposure to said camera.

* * * * *